(12) United States Patent
Swerev et al.

(10) Patent No.: US 8,158,848 B2
(45) Date of Patent: Apr. 17, 2012

(54) ABSORBENT SINGLE USE ARTICLE

(75) Inventors: Maximilian Swerev, Augsburg (DE);
Magnus Bodmer, Neu-Ulm (DE);
Fridmann Hornung, Lauchheim (DE);
Ruediger Kesselmeier, Herbrechtingen (DE)

(73) Assignee: Paul Hartmann AG, Heidenheim (DE)

( * ) Notice: Subject to any disclaimer, the term of this patent is extended or adjusted under 35 U.S.C. 154(b) by 1366 days.

(21) Appl. No.: 11/444,714

(22) Filed: Jun. 1, 2006

(65) Prior Publication Data

US 2006/0276765 A1    Dec. 7, 2006

Related U.S. Application Data

(60) Provisional application No. 60/687,184, filed on Jun. 3, 2005.

(51) Int. Cl.
*A61F 13/15* (2006.01)
*A61F 13/20* (2006.01)
*C09D 11/00* (2006.01)

(52) U.S. Cl. ............. 604/361; 604/358; 106/31.13

(58) Field of Classification Search ............. None
See application file for complete search history.

(56) References Cited

U.S. PATENT DOCUMENTS

| 3,675,654 | A | | 7/1972 | Baker et al. ............. 128/287 |
| 4,022,211 | A | * | 5/1977 | Timmons et al. ......... 604/361 |
| 4,834,733 | A | | 5/1989 | Huntoon et al. ......... 604/361 |
| 4,902,553 | A | * | 2/1990 | Hwang et al. ........... 428/156 |
| 5,035,691 | A | | 7/1991 | Zimmel et al. .......... 604/361 |
| 6,531,204 | B2 | * | 3/2003 | Suekane et al. ......... 428/156 |
| 6,710,221 | B1 | | 3/2004 | Pierce et al. ........... 604/361 |
| 2001/0053898 | A1 | * | 12/2001 | Olson et al. ........... 604/361 |
| 2002/0007162 | A1 | * | 1/2002 | Cammarota et al. ...... 604/361 |
| 2003/0073966 | A1 | * | 4/2003 | Sosalla et al. ......... 604/361 |
| 2003/0154904 | A1 | | 8/2003 | Klofta et al. .......... 116/206 |
| 2004/0064113 | A1 | | 4/2004 | Erdman ................ 604/361 |
| 2004/0138633 | A1 | * | 7/2004 | Mishima et al. ......... 604/361 |
| 2005/0096612 | A1 | | 5/2005 | Davis et al. ........... 604/361 |

FOREIGN PATENT DOCUMENTS

| DE | 88 12 048 U1 | 9/1988 |
| DE | 197 45 878 C1 | 10/1998 |
| EP | 0 211 524 A1 | 2/1987 |
| EP | 0 813 850 A2 | 5/1997 |
| WO | WO 99/16401 | 4/1999 |
| WO | WO 01/41691 A1 | 6/2001 |

OTHER PUBLICATIONS

German Patent Office Official Report dated Jan. 1, 2006, citing references and showing their degree of relevance accorded by the German Patent Office.
International Search Report dated Oct. 19, 2006.

* cited by examiner

*Primary Examiner* — Tatyana Zalukaeva
*Assistant Examiner* — Susan Su
(74) *Attorney, Agent, or Firm* — Young, Basile, Hanlon & MacFarlane, P.C.

(57) ABSTRACT

An absorbent single-use article includes an absorbent element for storing bodily fluids and a backsheet that is fluid impermeable, at least in sections. The fluid impermeable backsheet has a microporous breathable film. A moisture indicator is provided on the side of the film facing the absorbent element in the form of a visual perceptible textured arrangement applied directly to the film, wherein the textured arrangement detaches itself beyond recognition upon contact with aqueous fluid.

16 Claims, 6 Drawing Sheets

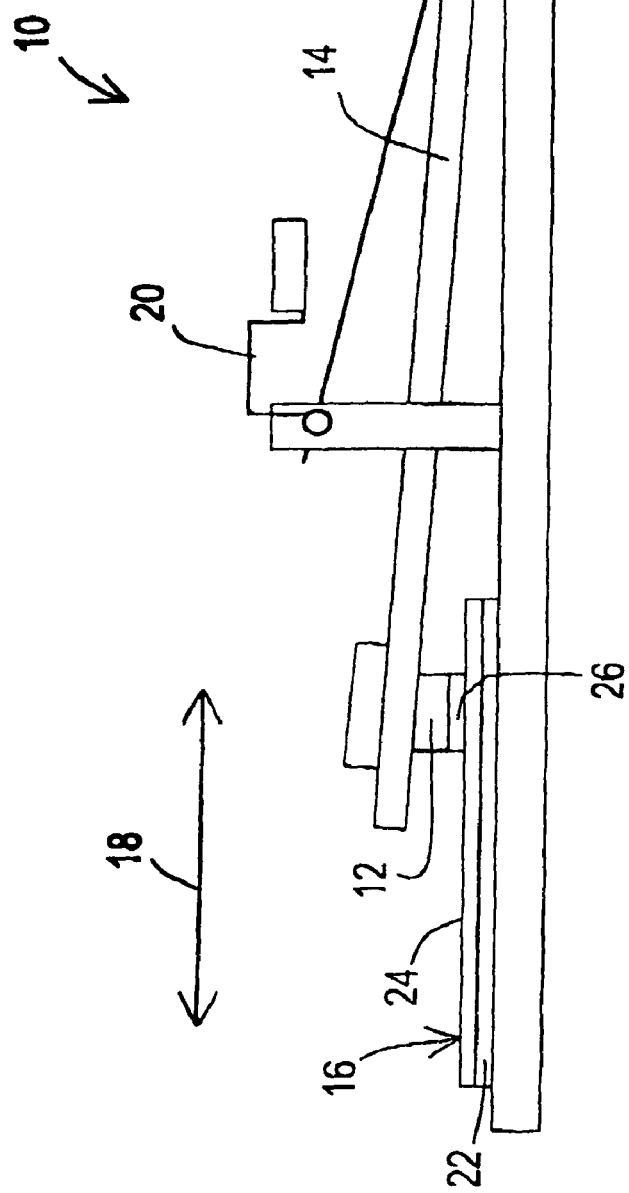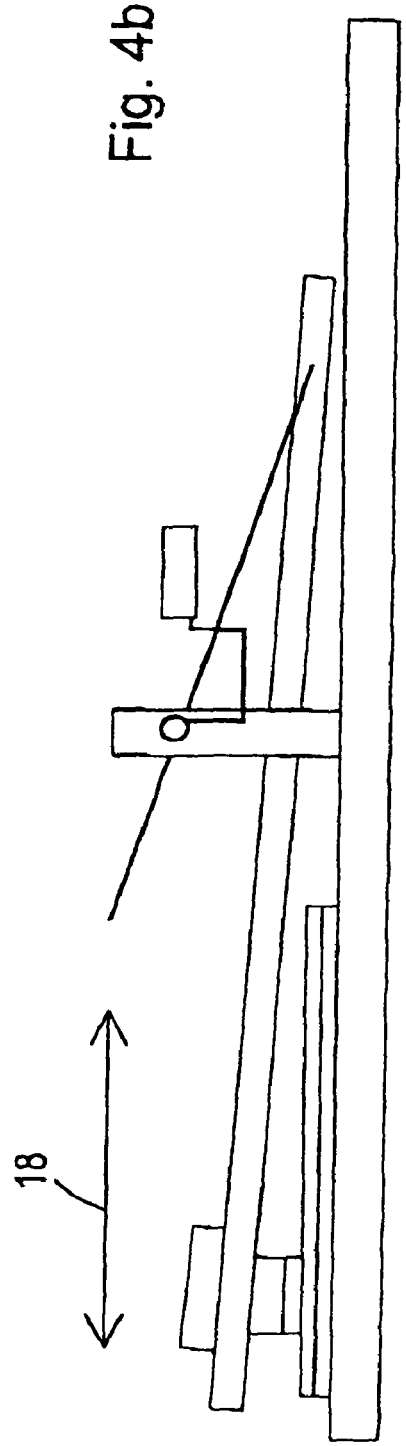

ABSORBENT SINGLE USE ARTICLE

CROSS-REFERENCE TO COPENDING APPLICATION

This application claims priority to the Jun. 3, 2005 filing date of co-pending U.S. Provisional Patent Application Ser. No. 60/687,184, the contents of which are incorporated herein in its entirety.

BACKGROUND

The invention relates to an absorbent single-use article an absorbent element for storing bodily fluids and a back sheet which is fluid impermeable at least in sections, where the fluid-impermeable is provided with a moisture indicator The need has long existed for indicating saturation of an absorbent single-use article by suitable means. Different moisture indicators for this have become known. The moisture indicators are provided predominantly in the area of the absorbent element and on the side of the absorbent element facing away from the body to indicate saturation of the absorbent element.

Moisture indicators are known based on pH indicators which, depending on the pH value, show a change in color when saturated with bodily fluids and indicate saturation. Such discoloration is frequently hard to distinguish with respect to the low contrast, for example, from yellow to pale blue. These pH indicators can, for example, be applied as part of a hotmelt compound (U.S. Pat. No. 5,035,691). The production of hotmelt moisture indicators and their application, mostly by means of slot nozzle application, is complicated.

In addition, moisture indicators based on water-soluble inks are known and described, for example, in EP 0 211 524 B1. Such moisture indicators are supposed to dissolve and disperse on contact with bodily fluids. They can be applied, for example, by printing units, specifically by ink-jet printing, to suitable components of the single-use article, specifically to its backing sheet. Thus EP 0 211 524 B1 describes the imprinting of an impermeable plastic film as the backing sheet with water-soluble dye, for example in the form of graphics which change under the effects of bodily fluid, specifically become blurred.

When moisture indicators of the last named variety are used with single-use articles having microporous breathable films as the back sheet, problems concerning visibility result. The microporous films are in general relatively opaque since, as a result of the air-filled pores, different changes in the index of refraction lead to high opacity (milkiness). In this respect it has already been proposed to post-treat the films in a suitable way thermally and/or mechanically and thereby achieve a reduction in the opacity, i.e., improved transparency (EP 0 553 808 B1).

On the other hand, there is a fundamental problem with the functioning of the moisture indicator when using such moisture indicators based on water-soluble systems, such as water-soluble inks, in conjunction with microporous breathable film materials. No satisfactory moisture indicators are known in conjunction with microporous breathable films. It has been proposed to apply the moisture indicator on or in the proximity of a strip, separate from the backsheet, said strip differing in color from the remaining backsheet material so that the location where the moisture indicator is applied is more easily identifiable to careworkers. However, the fundamental problem of the unsatisfactorily functioning moisture indicator on a water-soluble ink base was not solved.

Even in accordance with EP 0 813 850 A2, this fundamental problem of the inadequate functioning of such moisture indicators with microporous backsheets is not solved; instead the moisture indicator is applied to an additional layer separate from the backsheet, which raises production costs, reduces contrast and compromises recognizability.

It would, therefore, be desirable to provide a satisfactorily operating, simple and economical moisture indicator system for absorbent single-use articles with a breathable backsheet.

SUMMARY

An absorbent single-use article includes an absorbent element for storing bodily fluids, a backsheet which is fluid impermeable at least in sections, the fluid impermeable backsheet having a microporous breathable film, and on the side of the film facing the absorbent element, a moisture indicator is provided in the form of a visually perceptible textured arrangement applied directly to the film, the textured arrangement being detached beyond recognition upon contact with aqueous fluid.

The moisture indicator is applied to the film with a coating thickness of at least 2 µm, at least 5 µm, or at least 24 µm.

The moisture indicator is applied to the film with a dry weight of at least 0.00024 g/cm$^2$, at least 0.00049 g/cm$^2$, or at least 0.0024 g/cm$^2$.

The moisture indicator may include a dye with an $R_F$ value greater than 0.48. The dye can be taken from a group of azo dyes.

In the single-use article, the textured arrangement of the moisture indicator can be applied in the form of at least one of symbols, codes and characters.

The film may consist of a polymer selected from the group of polyethylenes and polypropylenes.

The film may contain calcium carbonate as an inorganic filler material. The calcium carbonate is contained in an amount of 30-80%, or 40-70% or 50-60% by weight relative to the mass of the film.

The film may be corona treated on an application side of the moisture indicator.

The film has a surface texture. The surface texture may be a surface stamping.

In the single-use article, a side of the film lying opposite the moisture indicator can be laminated with a non-woven material.

The film can be thermally laminated with the non-woven material. The file can also be thermally laminated with the non-woven material over its entire surface.

BRIEF DESCRIPTION

Additional features, advantages and details can be found in the appended claims and from the drawing and following description in which:

Figure 5:
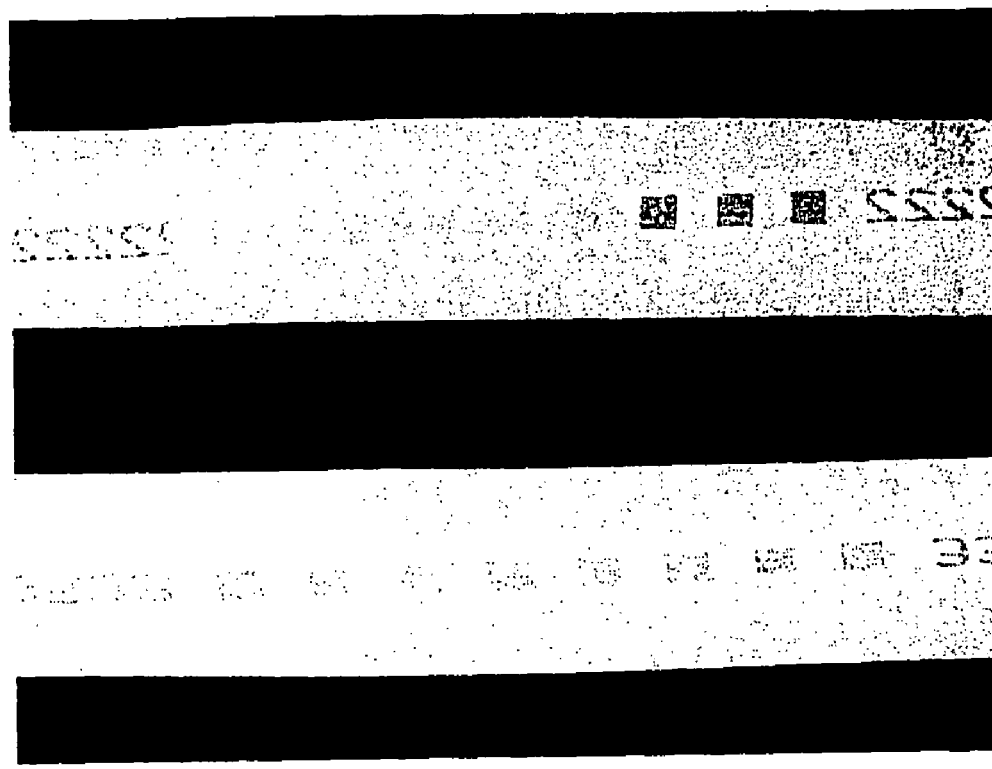
Figure 6:
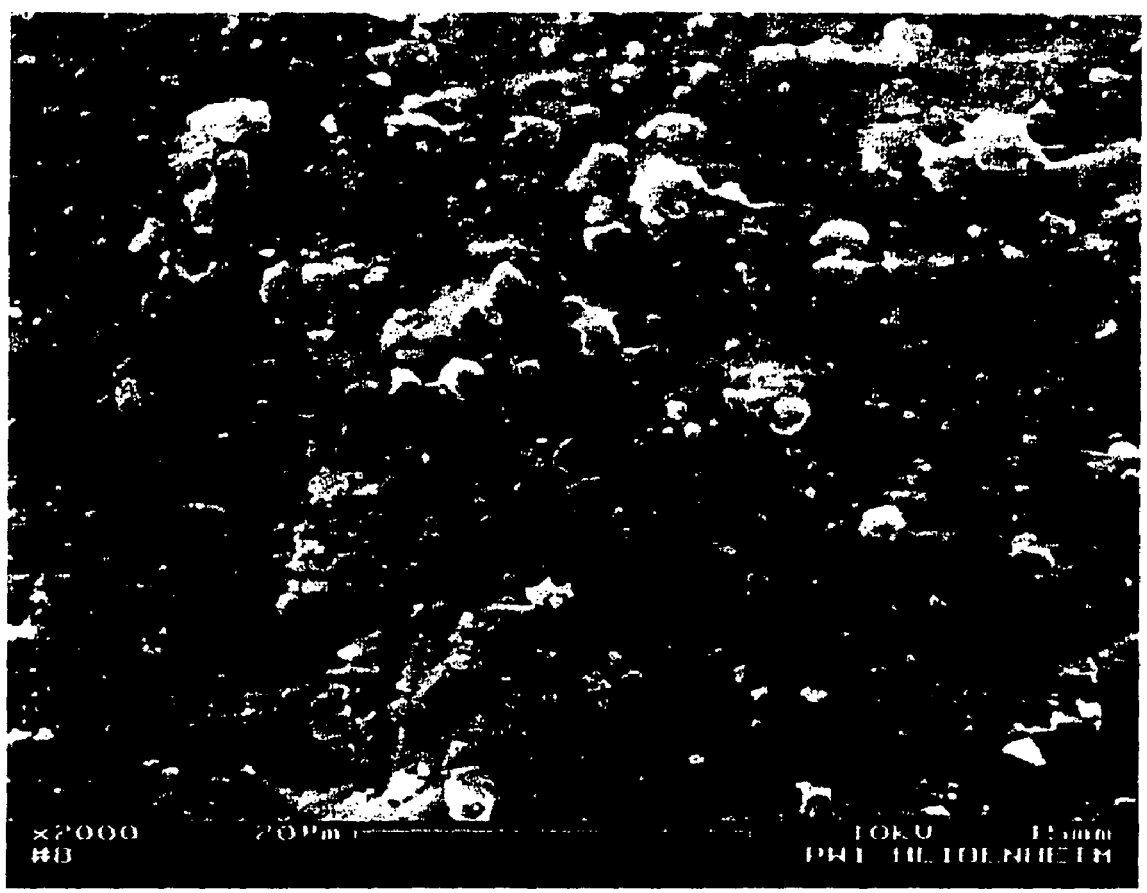

FIGS. 4a and b show two positions of a device for performing the wipe-off test;

FIG. 5 shows the result of performing a wipe-off test with two different moisture indicator systems; and FIG. 6 is a scanning electron microscope rendering of the surface of a microporous breathable film of the backsheet.

DETAILED DESCRIPTION

Figure 1:
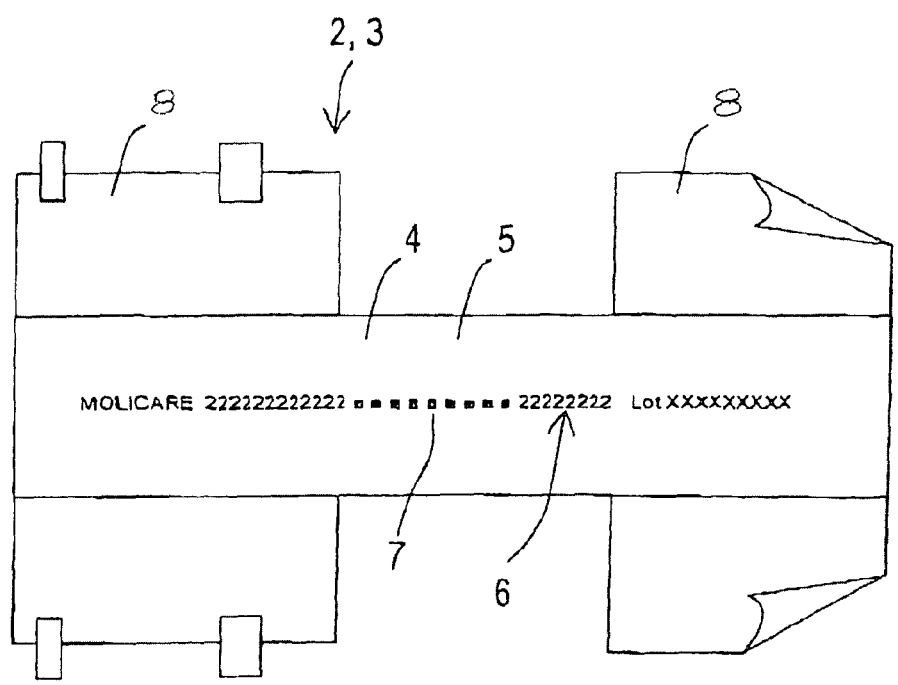
FIG. 1 is a schematic external view of an absorbent incontinence article with a moisture indicator.

FIG. 1 shows a plan view of the outside facing away from the body of a single-use article 2 in the form of an incontinence diaper 3. The incontinence diaper 3 comprises a main or chassis part 4 with a fluid impermeable, but microporous breathable backsheet 5 forming the outer visible side. Where desired or required the incontinence diaper can include suitable wings 8 connected to main or chassis part 4. The microporosity of the backsheet 5 is achieved by adding an inorganic filler material, specifically in the form of $CaCO_3$, to a film, specifically of polyolefin, and stretching the film of the backsheet 5. The incontinence diaper further comprises projecting side flaps to locate the diaper around the body of a user.

A textured arrangement 6 is applied directly on the inside of the backsheet 5 facing the body. The textured arrangement forms a visually perceptible moisture indicator 7 directly on the inner surface of the polymer film which is detachable in contact with bodily fluids. The composition of the moisture indicator is matched to the, in this case, polar surface of the film on the basis of polyolefins with an inorganic filler material, preferably $CaCO_3$, such that when impacted by fluid, the moisture indicator almost immediately detaches itself or dissolves into unrecognizability. This is visually recognizable immediately through the preferably transparent material of the backsheet. A scanning electron microscope rendering of the surface of the backsheet 5 facing the body is shown in FIG. 6. The electron microscope picture was taken at a voltage of 10 kV and is shown enlarged 2000 times with a scale of 20 µm added.

As the result of a moisture indicator being applied directly to a microporous breathable film as a textured arrangement in a visually perceptible form and detaching itself beyond recognition from this film when contacting aqueous fluid, there is a reliable indicator at all times of the single-use article being saturated.

The detachment of the visually perceptible textured arrangement of the moisture indicator from the film takes place when the product is correctly used, for example, when a diaper is appropriately saturated. The detachment of the visually perceptible textured arrangement of the moisture indicator from the film can also be determined by the wipe-off test which is explained in what follows.

Wipe-Off Test

This test is derived from the European standard EN ISO 105-X16:2002 (D) (color fastness tests), which is to determine color fastness in textiles to rubbing. In order to perform the wipe-off test, the equipment conforming to 4.1 of the standard is used, as shown schematically in FIG. 4. FIG. 4 shows the test equipment 10, by means of which a cylindrical test pin 12 under a specified standard pressure of 11.1.1 +/−0.5 N having a diameter of 16±0.1 mm is pulled back and forth on a test specimen 16 by means of an essentially horizontal pushrod 14. This back-and-forth motion is generated by a crank mechanism 20 in the direction of the double-ended arrow 18. The test specimen 16 is formed of a microporous breathable film material 22 forming the backsheet, on the surface of which a moisture indicator 24 was applied immediately and directly, specifically pressed on and dried by evaporating the solvent. On the side of the test pin 12 facing the test specimen 16 there is a standard cotton fabric 26 in the form of a standard cotton test sample in accordance with ISO 150-F: 1985 (obtainable from the Testex Company Test Materials, Bad Münstereifel, Germany). This standard cotton fabric was soaked in demineralized water such that water absorption of 95% to 100% exists in accordance with 6.3 of the standard.

To perform the wipe-off test, a back-and-forth motion is performed in the direction of the double-headed arrow by 18 means of the crank mechanism 20 and the result is then examined. If the previously applied moisture indicator 24 is blurred or wiped off beyond recognition, the system of moisture indicator 24 and backsheet 22 is suitable for the intended purpose.

The moisture indicator is specifically suitable if the moisture indicator is wiped off beyond recognition following the wipe test described in a maximum of 20 back-and-forth movements of the test pin 12, preferably in a maximum of 10 back-and-forth movements and, particularly preferably, in a maximum of 5 back-and-forth movements.

For example, FIG. 5 shows the result in the wipe test described with a system 1 (above) and with a system 2 (below). In the case of the system 1, the textured arrangement of the moisture indicator is blurred beyond recognition after five back-and-forth movements inside the area of the back-and-forth movement. In the case of the system 2 not in accordance with the invention, the textured arrangement of the moisture indicator is not blurred beyond recognition even after 50 back-and-forth movements of the test pin 12, but is still visually completely recognizable. The moisture indicator in system 1 is an ink used in the watch and clock industry with an azo dye and polyvinyl pyrrolidone as the binder polymer (obtainable as type 5533 from the Imaje Company, Stuttgart, Germany). The microporous breathable backsheet (model Hypor B 140 from the RKW Company, Wasserburg, Germany) is a non-woven/film laminate consisting of a microporous breathable film and a spun non-woven. The basis weight of the blown extruded polypropylene film is 20.5 $g/m^2$. The film stretched in the direction of the machine has a chalk percentage ($CaCO_3$) as the component providing the microporosity of 50 to 60% by weight relative to the mass of the film. The basis weight of the thermally surface-bonded laminate is 35 $g/m^2$, where the spun non-woven is applied to the side of the film facing away from the moisture indicator. The moisture indicator system (2) below is the standard moisture indicator FT 123 from the Imaje Company with a triphenylmethane dye, where the backsheet is the same as with the moisture indicator system 1 (above). Interaction between the moisture indicator and the microporous breathable film is such that even after 50 back-and-forth movements of the pressure body the textured arrangement of the moisture indicator remained recognizable almost unchanged although the standard moisture indicator Image FT 123 is described as water soluble.

Even if the functioning of moisture indicator systems has not been explained exhaustively, it has been established in what has been presented that a satisfactory response of the moisture indicator when saturated is to be attributed not only to the special chemical and physical properties of the microporous breathable film materials and to the chemical interaction between the film materials, which mostly comprise polyethylenes and/or polypropylenes, and the moisture indicator, but interactions with the inorganic fillers, generally $CaCO_3$, and possible geometric effects between the surface structure and/or pore structure of the microporous breathable film and the moisture indicator must also be taken into consideration. This has not been recognized previously.

As the result of a systematic observation of the possible interactions, and accordingly by specific selection of different microporous breathable film materials as backsheet components of a single-use article in combination with suitable ink-based moisture indicator systems, the potential for creating a functioning indicator system on this basis is created for the first time. It is not necessary to treat the film material in the area intended for the moisture indicator with additional coatings, nor to apply the moisture indicator on separate sheets of material. The direct application of the moisture indicator to the microporous breathable film of the backsheet in a suitable visually perceptible coating thickness, textured arrangement and contrast ensure the detection of the moisture indicator even with backsheets having microporous breathable film material. The moisture indicator (7) is provided in the form of a visually perceptible textured arrangement (6) applied directly to the film, as shown schematically in FIG. 1, where the textured arrangement becomes detached beyond recognition in contact with aqueous fluid. This achieves good visibility of the indication of the moisture indicator, which is advantageous in particular for older persons with diminished vision, but also for nursing staff, particularly while providing care during the night.

Absorbent, single-use articles are understood to include all articles intended for a single use whose function is to absorb bodily fluids, such as for example urine, watery stool, blood or exudate from a wound.

Absorbent single-use articles are, in particular, diapers and liners for babies, small children and incontinent adults.

In a further aspect, absorbent single-use articles are also understood to mean absorbent covers, for example, for the operating theater or dressings for wounds.

The fluid impermeable backsheet is understood to comprise the layer or composite layer which fulfils a barrier function for the bodily fluids on the side of the absorbent single-use article facing away from the body.

In accordance with one aspect, the textured arrangement of the moisture indicator is applied in the form of visually identifiable symbols, codes, numbers, letters or other abstract graphics. As a further advantage, the textured arrangement of the moisture indicator gives information about the single-use article, for example, product name, batch number, product size or absorbency.

The textured arrangement can be designed in blocks. In this way it can be ascertained immediately and without more ado when the textured arrangement becomes detached or dissolves upon contact with aqueous fluid.

The textured arrangement of the moisture indicator on the film can also be provided in the lengthwise direction. The moisture indicator is easily applied to the film such that when the absorbent article is worn by a person, the moisture indicator extends starting from the front area of the absorbent single-use article through the crotch to the rear area of the single-use article. The moisture indicator advantageously extends in its textured arrangement on the film over the length of the absorbent element provided in the single-use article. The moisture indicator is advantageously located on the film in an area which corresponds to the area of the absorbent element.

The textured arrangement of the moisture indicator is visually recognizable through the backsheet on the side facing away from the absorbent element by means of suitable contrasting. The composition of the moisture indicator contains at least one colorant. The colorant is taken from the group of dyes and pigments.

The moisture indicator can be a water-dispersible or water-removable and/or water-soluble dye.

It also proves to be advantageous if the moisture indicator is applied to the backsheet with a film thickness of at least 2 µm, in particular, of at least 5 µm and further, in particular, of 10 µm to 25 µm. The application of the moisture indicator in the form of dry weight is advantageously at least 0.00024 g/cm$^2$, in particular at least 0.00049 g/cm$^2$ and further, in particular, at least 0.0024 g/cm$^2$.

The interactions mentioned previously can be detected even more extensively by tests to be described in what follows; what is essential here is the interaction between visually perceptible components of the moisture indicator, in particular the dyes, with the surface of the microporous backsheet and its components, in particular the inorganic fillers through which, by stretching the film material in a known way, microporosity of the film is produced by loosening the previously firmly anchored fillers in the film composite which produces the microporosity in a known way. It was established that the polarity of the components of the moisture indicator on the one hand and the polarity of the backsheet, or its components, have a critically important significance with respect to the functioning of the moisture indicator. Microporous films have polar surfaces mostly from the addition of the $CaCO_3$ particles. If there is a high affinity in this regard of the moisture indicator for the substrate, the moisture indicator does not detach satisfactorily even when saturated, although water-solubility or dispersibility in aqueous fluids of the important components exists.

The inks normally used as the moisture indicating substance are low-viscosity compounds on a water and solvent base with a viscosity of 4 to 30 mPAs, often consisting of a mixture of organic solvents (up to eight components in some cases to control drying time) and comprising dyes. Ketones (preferably methylethylketone), acetates (esters), glycolethers and alcohols (e.g., ethanol) are used as solvents. The proportion of solvent is normally 80 to 90% (m/m). The colorants (3 to 4% m/m) are principally soluble dyes with high color fastness and thermal stability, in part pigments with a particle size less than 3 ÿm. The inks contain 5 to 15% artificial resins of one or more types of polymer as binders to control viscosity, drop formation and bonding of the colorants to the surface to be printed. The flow properties can be influenced by additives (less than 1% m/m) to ensure a specific droplet stream, they also work as softeners in the binder. A conductive salt is preferably also used to achieve an electrical conductivity of $>10^5$ ÿ- $cm^{-1}$ so that the ink droplets can be diverted in the electrical field to form an image.

In order to ensure the function of the moisture indicator, it was determined that the polarity of the dye used in combination with suitable types of polymers in the moisture indicator which, as binders, produce the adhesion to the substrate, that is the microporous breathable film material, can be adjusted optimally to the properties of this microporous breathable film material of the backsheet. A very good tool for evaluating the polarity of molecules is thin-layer chromatography (TLC) in the form of normal phase thin-layer chromatography. Here, the separation of a material on a stationary phase with a specific polarity is carried out in interaction with a mobile phase of a specific polarity: a separation on a polar stationary phase can be performed with a more non-polar solvent or solvent mixture of a specific eluotropy. The $R_F$ value is determined from the distance covered by a compound to be analyzed or of a material to be analyzed in proportion to the distance of the mobile phase, that is the actual separation distance. The $R_F$ value is a measure of the strength of the interaction of the material or compound with the stationary phase. The stronger the interaction with the substrate, that is the stationary phase, the less distance is the transportation with the eluant (mobile phase) on the stationary phase. Using the TLC system of a polar stationary phase with a non-polar mobile phase, dyes can be selected as moisture indicators which have the required low interaction with the polar functions of the breathable film. As was shown in the comparative studies of various inks from different manufacturers, ink dyes with a weak polar interaction can be distinguished in principle from inks with clearly stronger interaction.

It proves to be especially advantageous if a moisture indicator on a polar stationary phase in the form of a thin layer plate in accordance with the test method described in more detail of thin layer chromatography has an $R_F$ value greater than 0.48.

Many of the commonly known inks are based on triphenylmethane dyes which all have an $R_F$ value ÿ 0.48 and cannot be separated, or not adequately separated, on polar surfaces of microporous breathable film materials. On the other hand, if a moisture indicator with an $R_F$ value greater than 0.48 is used, for example from the group of azo dyes, this means that the interaction between moisture indicator, or the dye of the moisture indicator, and the polar substrate is not such that a separation or dissolution of the moisture indicator is prevented when impinged on by fluid, so that the moisture indicator works in a visually perceptible manner.

With the help of thin layer chromatography, moisture indicators, or the dyes used for them, can be selected which are basically suitable for this purpose in mostly polar microporous breathable film materials as the backsheet of an absorbent single-use article.

The aforementioned thin layer chromatography test is conducted as follows:

To perform thin layer chromatography, a 20×20 cm plate-like carrier of polyester film is used as the stationary phase and a layer of silica gel 60 (silica gel with an average pore size of 60 Å=6 nm) is applied to the polyester film. The layer of silica gel has a specific surface of about 500 m$^2$/g and a grain of 5 to 17 µm. A fluorescence indicator is added to it which fluoresces under UV light of 254 nm and gypsum as binder. The thickness of the layer of silica gel is 0.25 mm. A stationary phase constituted thus is available as "TLC-Ready Film Polygramm SIL G/UV$_{254}$," from the Macherey-Nagel Company, Düren, Germany.

Onto this stationary phase, in a strip 5 mm-wide and using an extremely precise application device, 5 µl of one or several test solutions is applied at the beginning of a separation distance 7 cm in length. A Linomat III application device from the CAMAG Company in Berlin, Germany can be used for this purpose. To produce the test solutions, a quantity of 200 mg of a dye preparation is diluted to a volume of 20 ml with ethanol 96% (denatured with 1% of methylethylketone) or another suitable solvent. The TLC plate is allowed to dry after the application of the test solutions.

The stationary phase thus prepared is placed upright in a double-trough chamber with a cover, filled and saturated with the mobile phase of nonpolar solvent or solvent mixture in order to perform an ascending separation process with chamber saturation. The mobile phase (synonymous with eluant) comprises (at 20° C.) the following reagents/compounds which are present in proportions of 50:10:10:10:

n butanol for analysis (50),
methanol for analysis (10),
ammonia solution 25% for analysis (10)
demineralized water (10).

The procedure is performed such that 5 µl of the diluted test solution is applied in a strip 5 mm wide on the stationary phase (TLC ready film). After about a 10-minute drying time, the stationary phase is placed in the double-trough chamber filled with eluant (mobile phase). Chromatography takes place in accordance with the preceding parameters at a temperature of 20° C. When the eluant (the solvent mixture) reaches the end of the separation distance which in the present form measures 7 cm, the stationary phase is removed from the chamber and air dried. In the chromatogram obtained thus the zone(s) of the dye(s) of the test solutions is/are visually recognizable. The $R_F$ value can be calculated from ratio of the migration distance of the dyes to the overall separation distance (7 cm).

Figure 2:
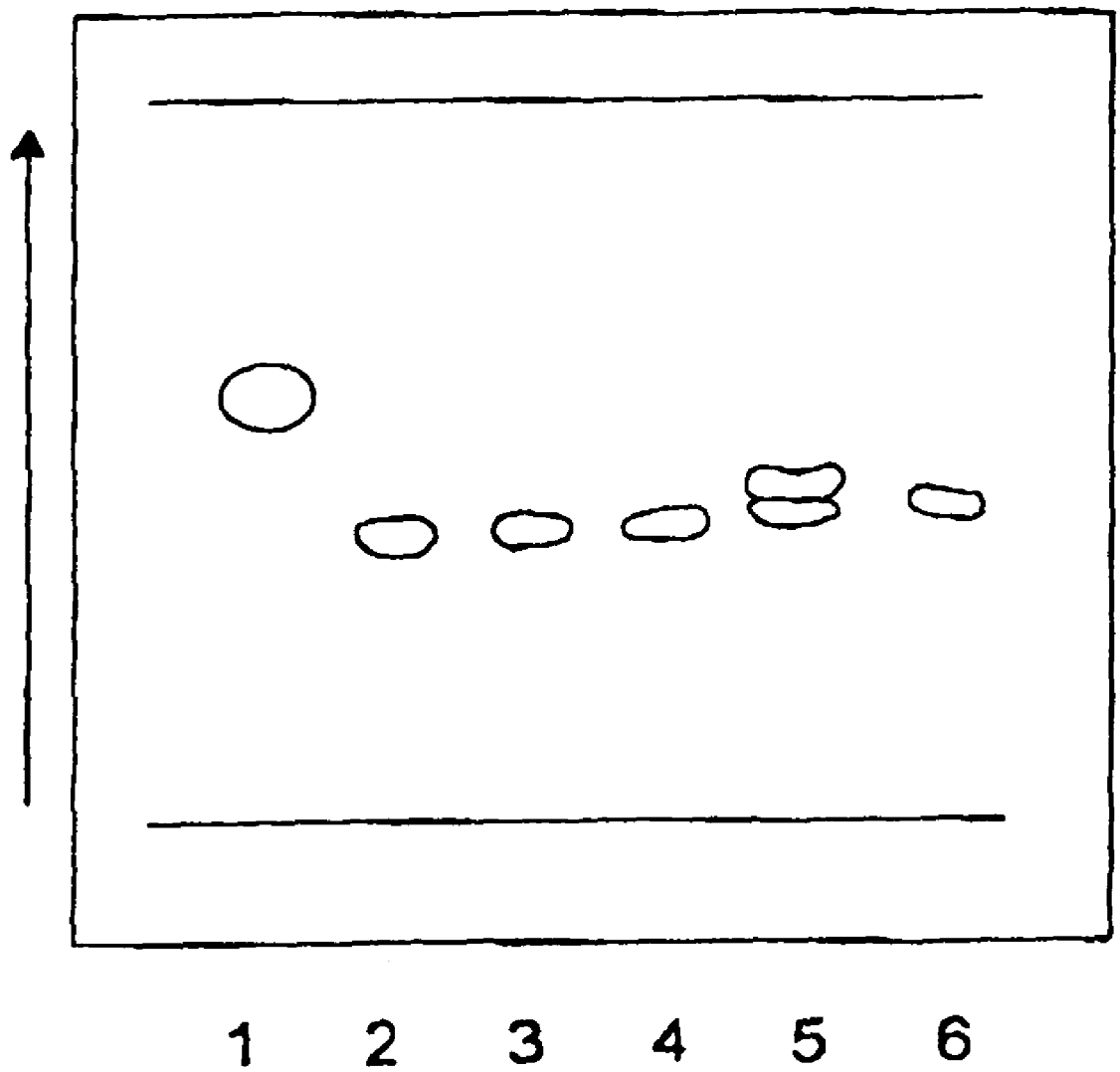
FIG. 2 is a schematic representation of a chromatogram of different moisture indicator systems.

FIG. 2 shows a chromatogram of a moisture indicator as described herein with an azo dye (1) and other moisture indicators based on triphenylmethane dyes. Separation occurs in the direction of the arrow indicated between the lower application zone (indicated by a lower horizontal line) and upper eluant front (indicated by the upper horizontal line). The moisture indicators (2)-(6) not in accordance with the invention based on triphenylmethane dyes all show an $R_F$ value less than 0.48. This means that the interactions between the dye of these moisture indicators and the strongly polar surface of the stationary phase (silica gel plate) are such that they adhere strongly to it and are difficult to separate under the effect of a relatively nonpolar solvent. The unique moisture indicator based on an azo dye however shows a mild tendency to adhere to the polar surface of the stationary phase.

It has proved to be advantageous if the dye of the moisture indicator comes from the group of azo dyes which have an $R_F$ value higher than 0.48 determined by the method described.

For a further test of whether the composition of the moisture indicator is suitable upon contact with aqueous fluid to ensure a detachment or dissolution beyond recognition of the visually perceptible textured arrangement, a modified "run-off test" on the model of the Edana run-off 152.1-02 is planned which is described in what follows.

Run-Off Test

Figure 3:
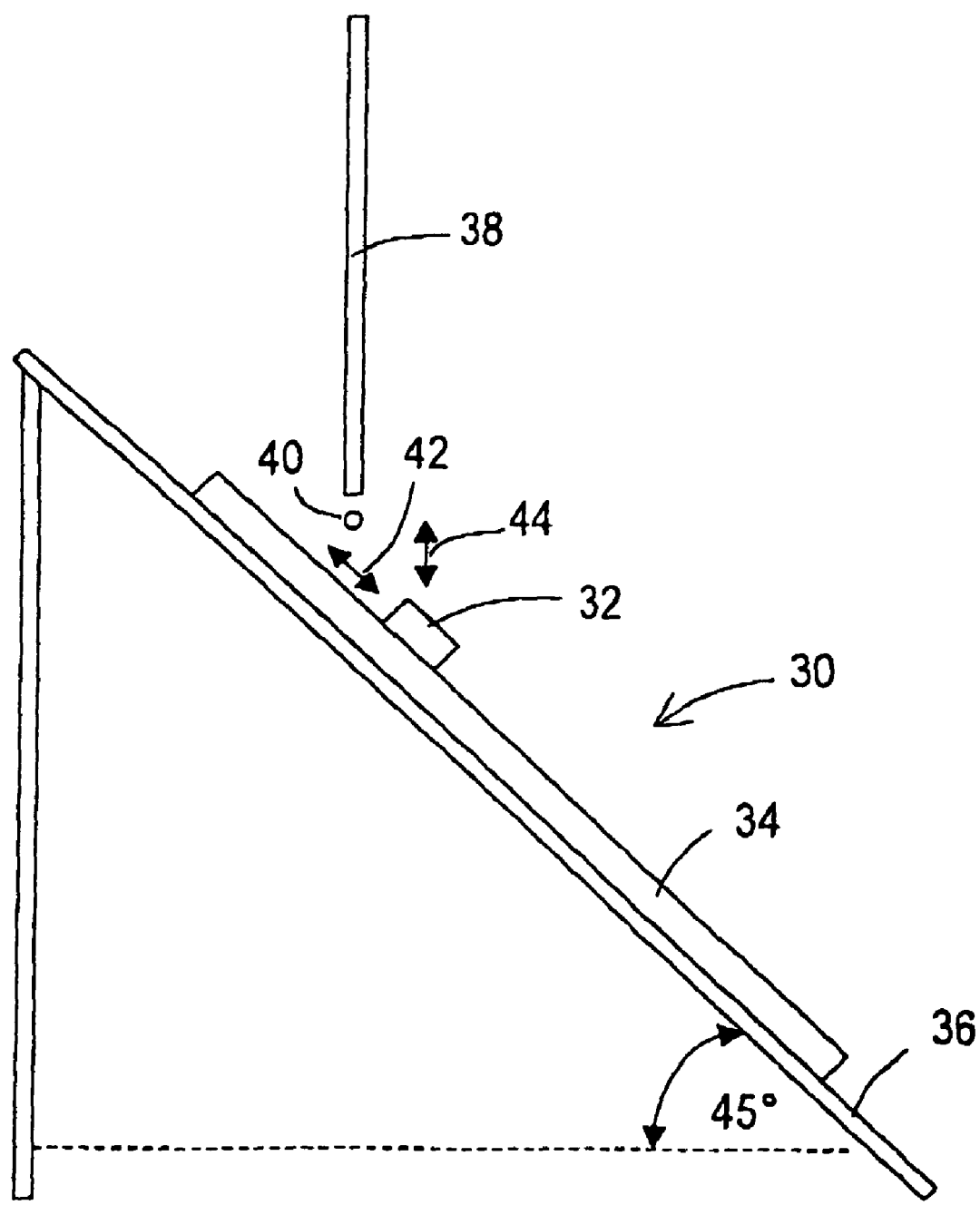
FIG. 3 is a depiction of the arrangement for performing the run-off test.

Using this test, it can be determined whether the composition of the moisture indicator is adequate for its intended use as a water-soluble moisture indicator. For the test, 1 µl of the ink to be tested (of the moisture indicator) 32 is applied to the microporous breathable film material 34 in question of the backsheet and allowed to dry so that the solvent of the moisture indicator can evaporate. Then a test specimen 30, which comprises the ink spot 32, is punched out and attached to a carrier plate with a sloping plane 36 which is inclined to the horizontal at 45° (see FIG. 3), and about 10 mm away in the direction of the plane from a contact point 42 for fluid which lies above it. At this contact point, aqueous fluid 40, specifically a 0.9%-NaCl solution, is dripped from a burette 38 at a speed of one drop per second onto the sloping plane from a distance of 10 mm (44) above the plane of the test specimen 30 so that this fluid runs off over the ink spot so that the separation of the ink can be observed visually and the volume of fluid required can be noted.

Moisture indicators, or the dyes in the moisture indicators, which cover a large migration distance when thin layer chromatography is performed and/or in particular are washed off without difficulty in the run-off test are a priori suitable for application to microporous, breathable films as moisture indicators.

It was ascertained that it proves advantageous if the dye for the moisture indicator comes from the group of azo dyes.

The microporous breathable film of the backsheet of the absorbent single-use article consists preferably of thermoplastic polymers. This film consists preferably of polyolefins, in particular preferably of polyethylene and/or polypropylene. LDPE (low-density polyethylene, LLDPE (linear low-density polyethylene) MDPE (medium-density polyethylene and/or HDPE (high-density polyethylene) and, analogously, different polypropylenes of varying thickness and copolymers, are used.

A single-use article in which the microporous breathable film contains calcium carbonate as an inorganic filler proves particularly advantageous. The amount of filler is advantageously 30 to 80 percent by weight, specifically 40 to 70 percent by weight and further specifically 50 to 60 percent by weight referenced to the mass of the film.

The microporous breathable films have, in particular, a basis weight of 8 g/m² to 25 g/m², preferably of from 10 g/m² to 18 g/m².

The microporous breathable films have breathability measured as water vapor permeability measured in accordance with DIN 53 122-1 (edition 2001-08) of at least 300 g/m²/24 hours, preferably of at least 500 g/m²/24 hours, further preferably of at least 1000 g/m²/24 hours.

The microporous breathable films have water impermeability, determined as a column of water under DIN EN 20811 (edition; German version EN 20811:1992) of at least 30 cm, particularly of at least 50 cm, preferably of at least 100 cm, further preferably of at least 150 cm.

In a further aspect, the average pore size of the microporous breathable film of the backsheet is 5 µm maximum, in particular, 3 µm maximum further, in particular, 1 µm maximum, and further, in particular, 0.5 µm. Determination of pore size can be made specifically with the help of a scanning electron microscope. The size of a single pore is understood to be the largest inside diameter of a pore detectable on the application side of the film. To calculate average pore size, the individual values are averaged arithmetically.

Advantageously the microporous breathable film, which is usually produced in a process of stretching the film to create the microporosity around the inorganic fillers, undergoes additional handing steps, as described in EP 0 768 168 B1, specifically the heating of the film web to preferably at least 70° C. and subsequent full-surface shock cooling on a pair of rollers comprising a rubber roller and stamping roller. The further treated film advantageously undergoes a subsequent zonal stretching over contoured pairs of rollers. This process is also known as the ring-rolling process. Ring-rolling can be carried out transversely or parallel to the direction of the machine.

It proves to be advantageous if the microporous breathable film is corona treated on the side facing the absorbent element. In particular a corona treatment is suitable which leads to a surface tension of 30 to 40, in particular of 32 to 38 and further in particular of 34 to 36 dyn at the film material. As the result of corona treatment, a film, in particular a polyolefin film, is conditioned for a coating procedure, in particular for printing. This is also suitable for the application of a moisture indicator of the type of interest here so that it adheres well on the one hand, but can be detached without difficulty and immediately when contacted by fluid.

In regard to suitable surface conditioning, it also proves to be advantageous if the microporous breathable film of the backsheet is given a very fine three-dimensional surface texture. This surface texture can be advantageously created in accordance with a procedure described in EP 0 768 168 B1 using a textural roller.

In a further advantageous embodiment of the absorbent single-use article, the fluid impermeable backsheet is a backsheet resembling a textile. The microporous breathable film is advantageously laminated with a non-woven on the side of the film facing away from the moisture indicator. The film is preferably thermally laminated with the non-woven. Thermal lamination can be carried using methods known to one skilled in the art (thermal sealing, air-through) The lamination of film to non-woven can be carried out on the basis of melt-point connections in a regular pattern. Further preferably the film is laminated thermally to the non-woven over the entire surface.

Any type of non-woven material can be used as the non-woven. Carded non-wovens are used preferably. Spunbond materials, spun non-wovens are further preferably used, in particular on the basis of polyolefins from the group of polypropylenes and polyethylenes. The non-wovens used have a basis weight of 8 g/m² to 25 g/m², preferably from 10 g/m² to 20 g/m².

The backsheet of the non-woven/film laminate has a total basis weight of 23 g/m², preferably at least 29 g/m², in particular preferably of at least 34 g/m².

What is claimed is:

1. An absorbent single-use article comprising:
an absorbent element for storing bodily fluids;
a backsheet which is fluid impermeable at least in sections, the fluid impermeable backsheet having a microporous breathable film, wherein the breathable film contains calcium carbonate as an organic filler material, the calcium carbonate present in an amount between 30% and 80% by weight relative to the mass of the breathable film; and wherein on the side of the film facing the absorbent element a moisture indicator is provided in the form of a visually perceptible textured arrangement applied by printing directly to the breathable film with a coating thickness of at least 2 µm, the moisture indicator including an azo dye with an $R_F$ value greater than 0.48, the textured arrangement being detached beyond recognition upon contact with aqueous fluid.

2. The single-use article of claim 1, wherein the moisture indicator is applied to the film with a coating thickness of at least 5 µm.

3. The single-use article of claim 2 but the moisture indicator is applied to the film with a coating thickness of at least 24 µm.

4. The single-use article of claim 1, wherein the moisture indicator is applied to the film with a dry weight of at least 0.00024 g/cm².

5. The single-use article of claim 1, wherein the moisture indicator is applied to the film with a dry weight of at least 0.00049 g/cm².

6. The single-use article of claim 1, wherein the moisture indicator is applied to the film with a dry weight of at least 0.0024 g/cm².

7. The single-use article of claim 1, wherein the textured arrangement of the moisture indicator is applied in the form of at least one of symbols, codes and characters.

8. The single-use article of claim 1, wherein the film consists of a polymer selected from the group of polyethylenes and polypropylenes.

9. The single-use article of claim 1, wherein calcium carbonate is contained in an amount of 40-70% by weight relative to the mass of the film.

10. The single-use article of claim 1, wherein calcium carbonate is contained in an amount of 50-60% by weight relative to the mass of the film.

11. The single-use article of claim 1, wherein the film is corona treated on an application side of the moisture indicator.

12. The single-use article of claim 1, wherein the film has a surface texture.

13. The single-use article of claim 12, wherein the surface texture is a surface stamping.

14. The single-use article of claim 1, wherein a side of the film lying opposite the moisture indicator is laminated with a non-woven material.

15. The single-use article of claim 14, wherein the film is thermally laminated with the non-woven material.

16. The single-use article of claim 14, wherein the film is thermally laminated with the non-woven material over its entire surface.

* * * * *